United States Patent
Sowa et al.

(10) Patent No.: US 8,268,339 B2
(45) Date of Patent: Sep. 18, 2012

(54) AGROCHEMICAL FORMULATIONS CONTAINING PYRROLIDONE ALKYLENE OXIDES

(75) Inventors: Christian Sowa, Neustadt (DE); Ulrich Steinbrenner, Neustadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/140,128

(22) PCT Filed: Dec. 10, 2009

(86) PCT No.: PCT/EP2009/066778
§ 371 (c)(1),
(2), (4) Date: Jun. 16, 2011

(87) PCT Pub. No.: WO2010/069848
PCT Pub. Date: Jun. 24, 2010

(65) Prior Publication Data
US 2011/0251061 A1    Oct. 13, 2011

(30) Foreign Application Priority Data
Dec. 19, 2008    (EP) .................................... 08172394

(51) Int. Cl.
*A01N 43/36* (2006.01)
*A61K 31/4015* (2006.01)
*C07D 207/267* (2006.01)

(52) U.S. Cl. ........ 424/405; 504/100; 504/283; 514/424; 548/551

(58) Field of Classification Search ........................ None
See application file for complete search history.

(56) References Cited

U.S. PATENT DOCUMENTS

| | | | |
|---|---|---|---|
| 3,823,160 A | | 7/1974 | Smith |
| 4,830,851 A | * | 5/1989 | Tracy et al. ................... 424/78.3 |
| 5,352,251 A | * | 10/1994 | Lin et al. ......................... 44/340 |

FOREIGN PATENT DOCUMENTS

| | | |
|---|---|---|
| EP | 0 785 297 | 7/1997 |
| GB | 930 668 | 7/1963 |
| WO | WO 88/06405 | 9/1988 |
| WO | WO 88/06585 | 9/1988 |
| WO | WO 94/22984 | 10/1994 |
| WO | WO 03/050211 | 6/2003 |

OTHER PUBLICATIONS

International Search Report prepared in International Application No. PCT/EP2009/066778, filed Dec. 10, 2009.
International Preliminary Report on Patentability from corresponding International Application No. PCT/EP2009/066778, filed Dec. 10, 2009.
Sidel'Kovskaya, F.P. et al., "A Study in the Field of Lactones and Lactams 12. Vinyl Ether of N-(β-Hydroxyethyl)-Pyrrolidone", Izvestia Akademii Nauk SSSR., (1958), pp. 1078-1084, vol. 9, Search Report.
Sidel'Kovskaya, F.P. et al., "Synthesis of N-β-Hydroxyethyl Lactams and Their Reaction with Thionyl Chloride", Izvestia Akademii Nauk SSSR., (1965), pp. 355-357, vol. 2, Search Report.

* cited by examiner

*Primary Examiner* — Jason M Nolan
*Assistant Examiner* — Michael Barker
(74) *Attorney, Agent, or Firm* — Brinks Hofer Gilson & Lione

(57) ABSTRACT

The present invention relates to a composition comprising pesticide and polyalkylene oxide. The invention furthermore relates to pyrrolidone alkylene oxides and the use thereof in agrochemical formulations. It furthermore relates to the use of the composition according to the invention for controlling phytopathogenic fungi and/or undesired vegetation and/or undesired attack by insects or mites and/or for regulating the growth of plants. Furthermore, it relates to the use of a composition according to the invention for controlling undesired attack by insects or mites on plants and/or for controlling phytopathogenic fungi and/or for controlling undesired vegetation, where seeds of useful plants are treated with the composition. Finally, the present invention also relates to seed treated with the composition according to the invention. The present invention comprises combinations of preferred features together with other preferred features.

18 Claims, No Drawings

AGROCHEMICAL FORMULATIONS CONTAINING PYRROLIDONE ALKYLENE OXIDES

This application is a National Stage application of International Application No. PCT/EP2009/066778, filed Dec. 10, 2009, the entire contents of which is hereby incorporated herein by reference. This application also claims priority under 35 U.S.C. §119 to European Patent Application No. 08172394.2, filed Dec. 19, 2008, the entire contents of which is hereby incorporated herein by reference.

The present invention relates to a composition comprising pesticide and polyalkylene oxide. The invention furthermore relates to pyrrolidone alkylene oxides and the use thereof in agrochemical formulations. It furthermore relates to the use of the composition according to the invention for controlling phytopathogenic fungi and/or undesired vegetation and/or undesired attack by insects or mites and/or for regulating the growth of plants. Furthermore, it relates to the use of a composition according to the invention for controlling undesired attack by insects or mites on plants and/or for controlling phytopathogenic fungi and/or for controlling undesired vegetation, where seeds of useful plants are treated with the composition. Finally, the present invention also relates to seed treated with the composition according to the invention. The present invention comprises combinations of preferred features together with other preferred features.

Pyrrolidone alkylene oxides are generally known:

WO 94/22984 discloses a fuel composition comprising hydrocarbons and additives. By way of example of an additive, there is prepared, inter alia, an adduct of 2-pyrrolidone and 20 1,2-epoxybutane units.

WO 03/050211 discloses an unleaded fuel comprising a fuel and an additive from the group of the pyrrolidone alkylene oxides.

U.S. Pat. No. 930,668 discloses acrylic esters of N-hydroxyalkyl lactams. Lactams with polyalklyene oxide groups may be employed for the preparation.

WO 88/06585 discloses pyrrolidonyl acrylate block polymers. Lactams with polyalklyene oxide groups may be employed for the preparation.

WO 88/06405 discloses iodine complexes with an alkylene oxide lactam and its use for disinfection.

GB 930668 discloses a hydroxyethoxyethoxyethylpyrrolidinone, which has been generated by reacting ethylene oxide and N-(2-hydroxyethyl)pyrrolidinone.

EP 0 785 297 discloses an aqueous acidic bath for the electrodeposition of copper coatings, which bath comprises copper salt, inorganic acid and a lactam alkoxylate (for example γ-butyrolactam hexaethoxylate).

An object of the present invention was to provide a pesticide-comprising composition which makes possible a high pesticide load while being stable. In this context, stable means that the composition and in particular the composition when diluted with water shows little tendency to crystallize, if any. Furthermore, it was an object that the abovementioned composition should show little tendency to crystallize, both in the case of dissolved and suspended pesticides. Furthermore, it was an object to provide a pesticide-comprising composition in the form of an emulsion concentrate which shows little tendency to crystallize.

The object was achieved by a composition comprising pesticide and polyalkylene oxide, the polyalkylene oxide corresponding to a pyrrolidone alkylene oxide of the formula I

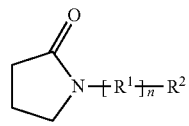

where $R^1$ is ethoxy, propoxy, butoxy and mixtures thereof;
$R^2$ is H and $C_1$-$C_6$-alkyl; and
n has a value from 2 to 20.
Here, the group

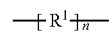

corresponds to an alkoxy polymer composed of n monomer units of the alkoxy group $R^1$. $R^1$ is ethoxy, propoxy, butoxy and their mixtures. This means that the alkoxy polymer can be a homopolymer of ethoxy, propoxy or butoxy or else a copolymer which is composed of at least two different monomers units of ethoxy, propoxy or butoxy. The copolymer can be a random mixed copolymer or a block copolymer, the copolymer is preferably a block copolymer. The term "block copolymer" means that the various monomer units occur in the polymer in each case in a block of identical monomer units, for example three ethoxy units, followed by five propoxy units, and then followed by two butoxy units.

The term "ethoxy" is —$CH_2$—$CH_2$—O, "propoxy" —$CH_2$—$CH(CH_3)$—O—, and "butoxy" —$CH_2$—CH($CH_2CH_3$)—O—. Such alkoxy units are generally known to the skilled worker, and corresponding alkoxy polymers can be obtained from the corresponding alkylene oxides such as ethylene oxide, propylene oxide and butylene oxide, for example by alkoxylation.

The index n can be within a certain range of values, for example 2 to 20. This means that not only integers such as 3, 4 or 5, but also values between integers, such as 3.15, may occur. The same also applies to the indices m, o and p.

$R^1$ is preferably butoxy and mixtures of butoxy with ethoxy and/or propoxy, particularly preferably butoxy and mixtures of butoxy with propoxy. $R^2$ is H and $C_1$-$C_6$-alkyl, preferably H and methyl, especially H. The index n has a value from 2 to 20, preferably 2 to 16, particularly preferably 3 to 14.

The composition according to the invention usually comprises at least 10% by weight, preferably at least 20% by weight, especially preferably at least 30% by weight, of pyrrolidone alkylene oxide I. In most cases, the composition comprises no more than 95% by weight, preferably no more than 90% by weight, especially preferably no more than 80% by weight, of pyrrolidone alkylene oxide I.

The composition according to the invention can be anhydrous or may comprise an aqueous phase, it is preferably anhydrous. In one embodiment, the composition is anhydrous. It usually comprises no more than 5% by weight, preferably no more than 2% by weight, especially preferably no more than 0.5% by weight and specifically no more than 0.1% by weight of water. In this embodiment, the composition comprises at least 40% by weight, preferably at least 50% by weight, especially preferably at least 60% by weight, of solvent system, based on the composition. The composition preferably comprises from 40 to 95% by weight, preferably at least from 50 to 90% by weight, especially preferably at least from 60 to 90% by weight, of solvent system, based on the composition.

In a further embodiment, the composition comprises an aqueous phase. Here, the composition comprises at least 5% by weight, preferably at least 10% by weight, especially preferably at least 20% by weight, of water, based on the composition. In this embodiment, the composition comprises at least 20% by weight, preferably at least 30% by weight, especially preferably at least 40% by weight, of solvent system, based on the composition.

The expression pesticide refers to at least one active substance selected from the group consisting of the fungicides, insecticides, nematicides, herbicides, safeners and/or growth regulators. Preferred pesticides are fungicides, insecticides and herbicides, in particular fungicides. Mixtures of pesticides of two or more of the abovementioned classes may also be used. The skilled worker is familiar with such pesticides, which can be found, for example, in Pesticide Manual, 14th Ed. (2006), The British Crop Protection Council, London. Suitable insecticides are insecticides from the class of the carbamates, organophosphates, organochlorine insecticides, phenylpyrazoles, pyrethroids, neonicotinoids, spinosins, avermectins, milbemycins, juvenile hormone analogs, alkyl halides, organotin compounds, nereistoxin analogs, benzoylureas, diacylhydrazines, METI acaricides, and insecticides such as chloropicrin, pymetrozine, flonicamid, clofentezine, hexythiazox, etoxazole, diafenthiuron, propargite, tetradifon, chlorfenapyr, DNOC, buprofezin, cyromazine, amitraz, hydramethylnon, acequinocyl, fluacrypyrim, rotenon, or their derivatives. Suitable fungicides are fungicides from the classes dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzylcarbamates, carbamates, carboxamides, carboxylic acid amides, chloronitriles, cyanoacetamide oximes, cyanoimidazoles, cyclopropanecarboxamides, dicarboximides, dihydrodioxazines, dinitrophenyl crotonates, dithiocarbamates, dithiolanes, ethylphosphonates, ethylaminothiazolecarboxamides, guanidines, hydroxy-(2-amino-)pyrimidines, hydroxyanilides, imidazoles, imidazolinones, inorganic substances, isobenzofuranones, methoxyacrylates, methoxycarbamates, morpholins, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiocarbamates, thiophanate, thiophenecarboxamides, toluamides, triphenyltin compounds, triazines, triazoles. Suitable herbicides are herbicides from the classes of acetamides, amides, aryloxyphenoxypropionates, benzamides, benzofuran, benzoic acids, benzothia-diazinones, bipyridylium, carbamates, chloroacetamides, chlorocarboxylic acids, cyclohexanediones, dinitroanilines, dinitrophenol, diphenyl ethers, glycines, imidazolinones, isoxazoles, isoxazolidinones, nitriles, N-phenylphthalimides, oxadiazoles, oxazolidinediones, oxyacetamides, phenoxycarboxylic acids, phenyl-carbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl (thio)benzoates, quinolinecarboxylic acids, semicarbazones, sulfonyl-aminocarbonyltriazolinones, sulfonyl ureas, tetrazolinones, thiadiazoles, thiocarbamates, triazines, triazinones, triazoles, triazolinones, triazolinones, triazolocarboxamides, triazolopyrimidines, triketones, uracils, ureas.

In one embodiment, the pesticide comprises an insecticide; preferably, the pesticide consists of at least one insecticide. In a further embodiment, the pesticide comprises a fungicide; preferably, the pesticide consists of at least one fungicide. Preferred fungicides are pyraclostrobin, metconazole and epoxyconazole. In a further embodiment, the pesticide comprises a herbicide; preferably, the pesticide consists of at least one herbicide. In a further embodiment, the pesticide comprises a growth regulator; preferably, the pesticide consists of at least one growth regulator.

In one embodiment, the pesticide is soluble in the pyrrolidone alkylene oxide to at least 10 g/l, preferably to at least 30 g/l and especially preferably to at least 50 g/l at 20° C. The solvent system employed here is the pyrrolidone alkylene oxide used in each case.

In a further embodiment, at least one pesticide is suspended in the solvent system in the form of solid particles to at least 90% by weight based on the pesticide. If the composition comprises at least two pesticides, at least one pesticide is dissolved in the solvent system to at least 90% by weight. Preferably, the pesticide is suspended in the solvent system to at least 95% by weight, especially preferably to at least 98% by weight.

The composition according to the invention usually comprises from 0.1 to 70% by weight of pesticide, preferably from 1 to 50% by weight, in particular from 3 to 30% by weight, based on the composition.

The composition according to the invention optionally comprises a surfactant, which means at least one surfactant. Surfactants are compounds which reduce the surface tension of water. Examples of surfactants are ionic (anionic or cationic) and nonionic surfactants. The composition preferably comprises at least two surfactants; especially preferably, it comprises one nonionic surfactant and one anionic surfactant. The weight ratio of nonionic to anionic surfactant is in most cases 1:5 to 5:1, preferably 1:3 to 3:1.

Suitable ionic surfactants are the alkali metal, alkaline earth metal and ammonium salts of aromatic sulfonic acids, for example of lignosulfonic acid (Borresperse® types, Borregaard, Norway), phenol-, naphthalene- (Morwet® types, Akzo Nobel, USA) and dibutylnaphthalenesulfonic acid (Nekal® types, BASF, Germany), and of fatty acids, alkyl- and alkylarylsulfonates, alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polycarboxylates (Sokalan® types, BASF, Germany) or phosphate esters of alkoxylated alcohols.

Preferred ionic surfactants are anionic surfactants. Suitable anionic surfactants are alkali metal and ammonium salts of alkyl sulfates (alkyl radical: $C_8$ to $C_{12}$), of sulfuric monoesters of ethoxylated alkanols (degree of ethoxylation from 4 to 30, alkyl radical: $C_{12}$ to $C_{18}$) and ethoxylated alkylphenols (degree of ethoxylation from 3 to 50, alkyl radical: $C_4$ to $C_{12}$), of alkylsulfonic acids (alkyl radical: $C_{12}$ to $C_{18}$) and of alkylarylsulfonic acids (alkyl radical: $C_9$ to $C_{18}$), or phosphate esters of an alkoxylated alcohol, specifically phosphate esters of an ethoxylated $C_{10-16}$-fatty alcohol with a degree of ethoxylation of from 3 to 15. Further anionic surfactants which are proved suitable are compounds of the general formula (I)

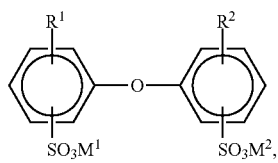

(I)

in which $R^1$ and $R^2$ are H atoms or $C_4$- to $C_{24}$-alkyl and are not simultaneously H atoms, and $M^1$ and $M^2$ can be alkali metal ions and/or ammonium ions. In the general formula (I), $R^1$ and $R^2$ are preferably linear or branched alkyl radicals having 6 to 18 C atoms, in particular 6, 12 and 16 C atoms, or hydrogen, where $R^1$ and $R^2$ are not both simultaneously H atoms. $M^1$ and $M^2$ are preferably sodium, potassium or ammonium, with sodium being especially preferred. Especially advantageous are compounds (I) in which $M^1$ and $M^2$ are sodium, $R^1$ is a branched alkyl radical having 12 C atoms and $R^2$ is an H atom or $R^1$. Frequently, technical mixtures are used which comprise 50 to 90% by weight of the monoalkylated product, such as, for example, Dowfax® 2A1 (brand of Dow Chemical Company). Preferred anionic surfactants are alkali metal and ammonium salts of alkylarylsulfonic acids (alkyl radical: $C_9$ to $C_{18}$), preferably linear or branched alkylbenzenesulfonic acids, and phosphate esters of an ethoxylated $C_{10-16}$-fatty alcohol with a degree of ethoxylation of from 3 to 15.

Suitable nonionic surfactants are polyoxyethylene octylphenol ethers, alkoxylated alcohols such as ethoxylated isooctyl-, octyl- or nonylphenol polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors, and proteins, denatured proteins, polysaccharides (for example methylcellulose), hydrophobically modified starches, polyvinyl alcohol (Mowiol® types, Clariant), polyalkoxylates, polyvinylamine (Lupamin® types, BASF SE), polyethyleneimine (Lupasol® types, BASF SE), polyvinylpyrrolidone, and their copolymers or block copolymers. A suitable alkoxylated alcohol is preferably a fatty alcohol which is alkoxylated with ethylene oxide (EO) or propylene oxide (PO), in particular one with 8 to 32, specifically with 9 to 18, carbon atoms in the fatty alcohol residue. The alkoxylated fatty alcohol usually has a degree of ethoxylation of from 1 to 30, preferably from 2 to 10 and specifically from 4 to 8 ethylene oxide groups and/or a degree of propoxylation of from 1 to 30, preferably from 2 to 15 and specifically from 3 to 10 propylene oxide groups. The block polymer is usually a di- or tri-block polymer or a derivative thereof, the polymeric moiety being composed of ethylene oxide and propylene oxide. The mean molar mass is usually at least 1000 g/mol, preferably at least 2000 g/mol. A substance which is specifically suitable is poly(ethylene oxide block propylene oxide) alkyl ether with a molar mass of at least 2000 g/mol and a $C_{1-10}$-alkyl ether unit. Preferred nonionic surfactants are alkylphenol polyglycol ethers, tristyryl-phenol ethoxylates, ethoxylated castor oil, preferably having in each case 10 to 40 ethylene oxide units per molecule.

The composition according to the invention can comprise further auxiliaries which are conventionally used for agrochemical formulations, the choice of the auxiliaries depending on the specific use form or the active substance. Examples of suitable auxiliaries are additional solvents, surface-active substances (such as solubilizers, protective colloids, wetters and adhesives), adjuvants, organic and inorganic thickeners, bactericides, antifoams, antifreeze agents, antifoams, colorants and stickers (for example for feed treatment).

Suitable additional solvents, which may be present in the solvent system as auxiliaries, are organic solvents such as mineral oil fractions of medium to high boiling point, such as kerosene and diesel oil, furthermore coal tar oils and oils of vegetable or animal origin, aliphatic, cyclic and aromatic hydrocarbons, for example paraffins, tetrahydronaphthalene, alkylated naphthalenes and their derivatives, alkylated benzenes and their derivatives, alcohols such as methanol, ethanol, propanol, butanol and cyclohexanol, glycols, ketones such as cyclohexanone, gamma-butyrolactone, dimethyl fatty acid amides, fatty acids and fatty acid esters, and strongly polar solvents, for example amines such as N-methylpyrrolidone. In principle, it is also possible to use solvent mixtures. It is preferred to add, to the composition according to the invention, no more than 30% by weight, preferably no more than 10% by weight, in each case based on the solvent system, and particularly preferably no additional solvents.

Suitable surface-active substances (adjuvants, wetters, stickers, dispersants or emulsifiers) in addition to the abovementioned surfactants are the alkali metal, alkaline earth metal and ammonium salts of aromatic sulfonic acids, for example of ligno-sulfonic acid (Borresperse® types, Borregaard, Norway), phenol-, naphthalene-(Morwet® types, Akzo Nobel) and dibutylnaphthalenesulfonic acid (Nekal® types, BASF), and of fatty acids, alkyl- and alkylarylsulfonates, alkyl sulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl polyglycol ethers, tributylphenyl polyglycol ethers, alkylaryl polyether alcohols, isotridecyl alcohol, fatty alcohol/ ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors, and proteins, denatured proteins, polysaccharides (for example methylcellulose), hydrophobically modified starches, polyvinyl alcohol (Mowiol® types, Clariant), polycarboxylates (Sokalan® types, BASF), polyalkoxylates, polyvinylamine (Lupamin® types, BASF), polyethyleneimine (Lupasol® types, BASF SE), polyvinylpyrrolidone, and their copolymers.

The emulsion according to the invention can comprise large amounts of surface-active substances and surfactant. It can comprise a total amount of from 0.1 to 40% by weight, preferably from 1 to 30 and in particular from 2 to 20% by weight of surface-active substances and surfactants, based on the total amount of the composition.

Examples of adjuvants are organically modified polysiloxanes such as BreakThruS 240®; alcohol alkoxylates such as Atplus®245, Atplus®MBA 1303, Plurafac®LF and Lutensol® ON; EO/PO block polymers, for example Piuronic® RPE 2035 and Genapol® B; alcohol ethoxylates, for example Lutensol® XP 80; and sodium dioctylsulfosuccinate, for example Leophen® RA.

Examples of thickeners (i.e. compounds which impart to the composition a modified flow behavior, i.e. high viscosity at rest and low viscosity in motion) are polysaccharides and organic and inorganic layer minerals such as xanthan gum (Kelzan®, CP Kelco), Rhodopol® 23 (Rhodia) or Veegum® (R.T. Vanderbilt) or Attaclay® (Engelhard Corp.).

Bactericides may be added to stabilize the composition. Examples of bactericides are those based on dichlorophen and benzyl alcohol hemiformal (Proxel® from ICI or Acticide® RS from Thor Chemie and Kathon® MK from Rohm & Haas) and isothiazolinone derivatives such as alkylisothiazolinones and benzoisothiazolinones (Acticide® MBS from Thor Chemie).

Examples of suitable antifreeze agents are ethylene glycol, propylene glycol, urea and glycerol.

Examples of antifoams are silicone emulsions (such as, for example Silikon® SRE, Wacker, Germany or Rhodorsil®, Rhodia, France), long-chain alcohols, fatty acids, salts of fatty acids, organofluorine compounds and their mixtures.

Examples of colorants are both pigments, which are sparingly soluble in water, and dyes, which are soluble in water. Examples which may be mentioned are the dyes and pigments known by the names Rhodamin B, C. I. Pigment Red 112 and C. I. Solvent Red 1, Pigment Blue 15:4, Pigment Blue 15:3, Pigment Blue 15:2, Pigment Blue 15:1, Pigment Blue 80, Pigment Yellow 1, Pigment Yellow 13, Pigment Red 48:2, Pigment Red 48:1, Pigment Red 57:1, Pigment Red 53:1, Pigment Orange 43, Pigment Orange 34, Pigment Orange 5, Pigment Green 36, Pigment Green 7, Pigment White 6, Pigment Brown 25, Basic Violet 10, Basic Violet 49, Acid Red 51, Acid Red 52, Acid Red 14, Acid Blue 9, Acid Yellow 23, Basic Red 10, Basic Red 108.

Examples of stickers are polyvinylpyrrolidone, polyvinyl acetate, polyvinyl alcohol and cellulose ethers (Tylose®, Shin-Etsu, Japan).

Compositions according to the invention are usually present in the form of agrochemical formulations. Suitable agrochemical formulations are water-soluble concentrates (SL, LS), dispersible concentrates (DC), emulsifiable concentrates (EC), emulsions (EW, EO, ES, ME), suspensions (SC, OD, FS) or suspoemulsions (SE). The composition is preferably present in the form of an emulsifiable concentrate (EC).

In most cases, the composition according to the invention is diluted prior to use in order to prepare what is known as the tank mix. Substances which are suitable for the dilution are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydro-naphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone or water. It is preferred to use water. The dilute composition is usually applied by spraying or atomizing. Immediately before use (tank mix), oils of various types, wetters, adjuvants, herbicides, bactericides, fungicides may be added to the tank mix. These agents can be admixed with the compositions according to the invention in the weight ratio 1:100 to 100:1, preferably 1:10 to 10:1. The pesticide concentration in the tank mix can be varied in substantial ranges. In general, it is between 0.0001 and 10%, preferably between 0.01 and 1%. When used in plant protection, the application rates are between 0.01 and 2.0 kg of active substance per ha, depending on the nature of the desired effect.

The present invention also relates to the use of a composition according to the invention for controlling phytopathogenic fungi and/or undesired vegetation and/or undesired attack by insects or mites and/or for regulating the growth of plants, where the composition is allowed to act on the respective pests, their environment or the plants to be protected from the respective pests, on the soil and/or undesired plants and/or the useful plants and/or their environment. The invention furthermore relates to the use of a composition according to the invention for controlling undesired attack by insects or mites on plants and/or for controlling phytopathogenic fungi and/or for controlling undesired vegetation, where seeds of useful plants are treated with the composition.

Furthermore, the invention relates to seed which has been treated with a composition according to the invention. The treatment (also referred to as seed dressing) results in the composition remaining on the seed. Preferably, the seed comprises the composition according to the invention. This composition can be applied to the seed in undiluted or, preferably, diluted form. Here, the composition in question can be diluted by a factor of 2 to 10, so that from 0.01 to 60% by weight, preferably from 0.1 to 40% by weight, of pesticide are present in the compositions to be used for dressing the seed. The application can take place before sowing. The treatment of plant propagation material, in particular the treatment of seed, is known to the skilled worker and is carried out by dusting, coating, pelleting, dipping or soaking the plant propagation material, the treatment preferably being effected by pelleting, coating and dusting, so that, for example, premature germination of the seed is prevented. In the treatment of seed, one will generally use pesticide amounts of from 1 to 1000 g/100 kg, preferably from 5 to 100 g/100 kg propagation material or seed.

The present invention also relates to a process for the preparation of a composition according to the invention, wherein a pesticide and a pyrrolidone alkylene oxide I are mixed. Preferred pyrrolidone alkylene oxides I and solvents are as described above. Mixing is effected by customary mixing processes, such as stirring, shaking or supplying energy in other forms. Further auxiliaries which are employed for the preparation of agrochemical formulations can be added in customary amounts. Examples of suitable auxiliaries are as described above.

The present invention furthermore relates to pyrrolidone alkylene oxides of the formula II

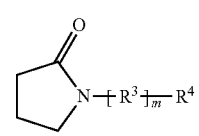

where $R^3$ is propoxy;
$R^4$ is H and $C_1$-$C_6$ alkyl; and
m has a value of from 2 to 6.

The index m preferably has a value from 3 to 5. $R^4$ is preferably H and methyl, specifically H.

The invention furthermore relates to pyrrolidone alkylene oxides of the formula III

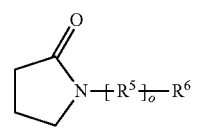

where $R^5$ is mixtures of ethoxy and propoxy;
$R^6$ is H and $C_1$-$C_6$ alkyl; and
o has a value of from 2 to 12.

The index o preferably has a value of from 2 to 10, especially preferably from 3 to 8 and specifically from 3 to 6. $R^4$ is preferably H and methyl, specifically H.

Here, the group

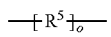

corresponds to an alkoxy polymer which is composed of n monomer units of the alkoxy group $R^5$. $R^5$ is mixtures of ethoxy and propoxy. This means that the alkoxy polymer is a copolymer which is composed of ethoxy and propoxy. The copolymer can be a random mixed copolymer or a block copolymer, the copolymer is preferably a block copolymer.

The invention furthermore relates to pyrrolidone alkylene oxides of the formula IV

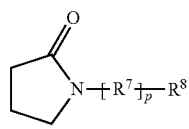

where $R^7$ is butoxy and mixtures of butoxy with ethoxy and/or propoxy;

$R^8$ is H and $C_1$-$C_6$ alkyl; and p has a value of from 2 to 18.

The index p preferably has a value of from 2 to 18, especially preferably from 2 to 14 and specifically from 3 to 12. $R^4$ is preferably H and methyl, specifically H.

Here, the group

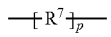

corresponds to an alkoxy polymer which is composed of n monomer units of the alkoxy group $R^7$. $R^7$ is butoxy and mixtures of butoxy with ethoxy and/or propoxy. This means that the alkoxy polymer can be a homopolymer of butoxy or else a copolymer which is composed of butoxy with ethoxy, butoxy with propoxy, or butoxy with ethoxy and with propoxy. The copolymer can be a random mixed copolymer or block copolymer, the copolymer is preferably a block copolymer, for example a diblock copolymer or a triblock copolymer.

The pyrrolidone alkylene oxides of the formulae II, III and IV can be prepared by alkoxylation of pyrrolidone. Substances which can be used for the alkoxylation are ethylene oxide, propylene oxide and butylene oxide. The alkoxylation can be catalyzed by strong bases, such as alkali metal hydroxides and alkaline earth metal hydroxides, Brönsted acids or Lewis acids, such as $AlCl_3$, $BF_3$. Catalysts such as hydrotalcite or double-metal cyanide (DMC) may be used for alcohol oxylates with a narrow distribution. The alkoxylation is preferably carried out at temperatures of from approximately 90 to 240° C., especially preferably from 110 to 190° C. The alkylene oxide or the mixture of a variety of alkylene oxides is pyrrolidone and catalyst charged under the vapor pressure of the alkylene oxide mixture which prevails at the selected reaction temperature, or at a higher pressure. If desired, the alkylene oxide can be diluted with an inert gas (for example noble gases, nitrogen, $CO_2$) up to 99.9%. In particular in the case of ethylene oxide, this additionally safeguards against gas-phase disintegration of this alkylene oxide, it also being possible, in this embodiment, to use a further alkylene oxide, for example propylene oxide, as inert gas within the meaning of the invention. Suitable alkoxylation conditions are also described in Nikolaus Schönfeldt, Grenzflächenaktive Äthylenoxid-Addukte, Wissenschaftliche Verlagsgesellschaft mbH, Stuttgart 1984. As a rule, the alkoxylation is carried out in the presence of the catalyst without addition of a solvent. However, the alkoxylation can also be carried out with the concomitant use of a solvent which is inert under the alkoxylation conditions.

In a suitable embodiment, the alkoxylation is catalyzed by at least one strong base. Examples of suitable strong bases are alkali metal alkoxides, alkali metal hydroxides, alkaline earth metal oxides or alkaline earth metal hydroxides. As a rule, the bases are employed in an amount of from 0.01 to 1% by weight based on the amount of pyrrolidone to be alkoxylated (cf. G. Gee et al., J. Chem. Soc.(1961), p. 1345; B. Wojtech, Makromol. Chem. 66, (1966), p. 180). An acid catalysis of the alkoxylation reaction is also possible. Besides Brönsted acids, Lewis acids such as, for example, $AlCl_3$, $BF_3$, $BF_3$-dietherates, $BF_3 \times H_3PO_4$, $SbCl_4 \times 2\ H_2O$, hydrotalcite (cf. P. H. Plesch, The Chemistry of Cationic Polymerization, Pergamon Press, New York (1963)) are also suitable.

The present invention also relates to the use of the pyrrolidone alkylene oxide of the above-described formulae II, II and IV in agrochemical formulations. Agrochemical formulations are known to the skilled worker. They usually comprise a pesticide and, optionally, auxiliaries for agrochemical formulations, for example the abovementioned auxiliaries for agrochemical formulations.

The pyrrolidone alkylene oxides of the formulae II, III and IV, especially III and IV, and very especially IV, are particularly suitable as polyalkylene oxide in the composition according to the invention.

Advantages of the present invention are, inter alia, that it makes possible a composition with a high pesticide load while being stable. The composition and the composition diluted with water show little tendency to crystallize, if any. The composition is suitable both for dissolved and for suspended pesticides and in both cases shows little tendency to crystallize. Compositions in the form of emulsion concentrates, in particular, are stable and do not tend to crystallize.

The examples which follow illustrate the invention, without limiting it.

EXAMPLES

Surfactant 1: Tristyrylphenol ethoxylate with 16 mol of ethylene oxide per mole (commercially available as Soprophor® BSU from Rhodia S.A.).

Surfactant 2: Calcium dodecylbenzenesulfonate (commercially available as Calsogen® AR 100 ND from Clariant).

Surfactant 3: Dodecylbenzenesulfonic acid, calcium salt (commercially available as Wettol® EM 1 from BASF).

Surfactant 4: nonionic surfactant based on ethoxylated castor oil (commercially available as Wettol® EM 31 from BASF).

Epoxyconazole: purity 95.5% by weight

Metconazole: purity 98.8% by weight

Pyraclostrobin: purity 99.4% by weight

Example 1 A

Pyrrolidone+3 Butylene Oxide (BuO)

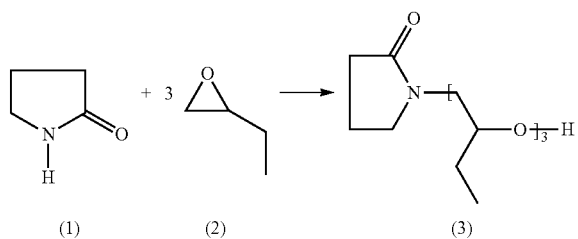

170.2 g (2.0 mol) of pyrrolidone (1) and 2.4 g of potassium hydroxide (50% by weight in water) were dehydrated for 2 h at 90° C. and 20 mbar. Thereafter, the mixture was transferred into a pressurized reactor, the pressure was brought to 1.5 bar using nitrogen, and 432.0 g (6.0 mol) of butylene oxide (2) were metered in at 130° C. in the course of 4 h at a pressure of no more than 3.3 bar. After stirring had been continued for 10 h, the mixture was allowed to cool to 80° C. and, while stirring, was flushed with nitrogen. The brown discharge was brought to pH 5.7 using approximately 3.3 g of acetic acid (1% by weight in water) so that 608.9 g of a pale brown, clear product (3) with a yield of 100% were formed.

Example 1 B

Pyrrolidone+4 Butylene Oxide

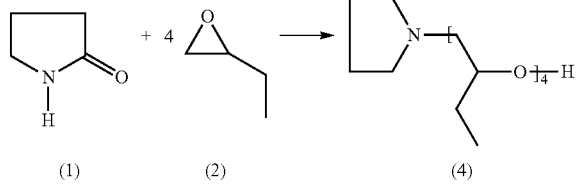

170.2 g (2.0 mol) of pyrrolidone (1) and 2.98 g of potassium hydroxide (50% by weight in water) were dehydrated for 2 h at 90° C. and 20 mbar. Thereafter, the mixture was transferred into a pressurized reactor, the pressure was brought to 1.5 bar using nitrogen, and 576.0 g (8.0 mol) of butylene oxide (2) were metered in at 130° C. in the course of 5 h at a pressure of no more than 3.5 bar. After stirring had been continued for 10 h, the mixture was allowed to cool to 80° C. and, while stirring, was flushed with nitrogen. The brown discharge was brought to pH 5.6 using approximately 3.7 g of acetic acid (1% by weight in water) so that 748 g of a pale brown, clear product (4) with a yield of 100% were formed.

Example 1 C

Pyrrolidone+5 Butylene Oxide

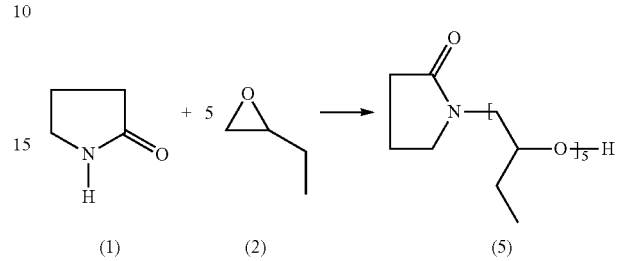

136.2 g (1.6 mol) of pyrrolidone (1) and 2.84 g of potassium hydroxide (50% by weight in water) were dehydrated for 2 h at 90° C. and 20 mbar. Thereafter, the mixture was transferred into a pressurized reactor, the pressure was brought to 1.5 bar using nitrogen, and 576.0 g (8.0 mol) of butylene oxide (2) were metered in at 130° C. in the course of 4 h at a pressure of no more than 3.7 bar. After stirring had been continued for 10 h, the mixture was allowed to cool to 80° C. and, while stirring, was flushed with nitrogen. The brown discharge was brought to pH 5.5 using approximately 3.3 g of acetic acid (1% by weight in water) so that 698 g of a pale brown, clear product (5) with a yield of 98% were formed.

Example 1 D

Pyrrolidone+5 Propylene Oxide+1 Butylene Oxide

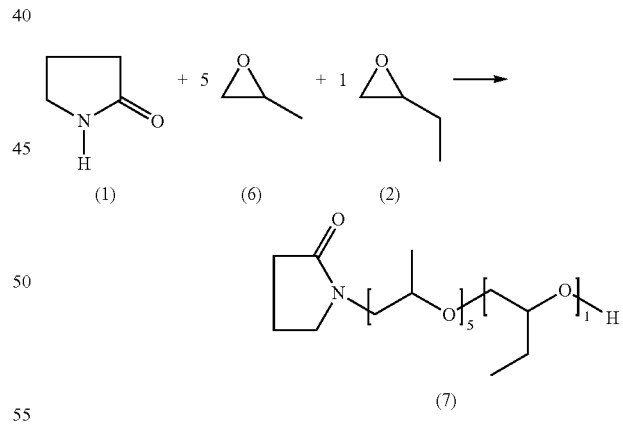

170.2 g (2.0 mol) of pyrrolidone and 3.58 g of potassium hydroxide (50% by weight in water) were dehydrated for 2 h at 90° C. and 20 mbar. Thereafter, the mixture was transferred into a pressurized reactor, the pressure was brought to 1.5 bar using nitrogen, and 581.0 g of propylene oxide (6) (10.0 mol) were metered in at 130° C. in the course of 5 h at a pressure of no more than 3.7 bar. Thereafter, 144.0 g (2.0 mol) of butylene oxide were metered in at 130° C. in 1 h at a pressure of no more than 3.9 bar. After stirring had been continued for 6 h, the mixture was allowed to cool to 80° C. and, while stirring, was flushed with nitrogen. The brown discharge was brought to pH 5.5 using approximately 1.9 g of acetic acid (1% by weight in water) so that 904 g of a pale brown, clear product (7) with a yield of 100% were formed.

Example 1 E

Pyrrolidone+10 Propylene Oxide+1 Butylene Oxide

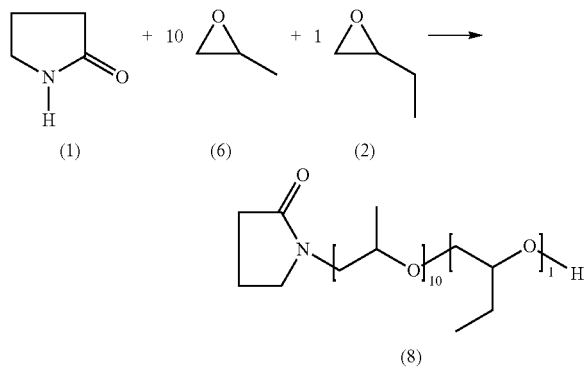

85.1 g (1.0 mol) of pyrrolidone and 2.96 g of potassium hydroxide (50% by weight in water) were dehydrated for 2 h at 90° C. and 20 mbar. Thereafter, the mixture was transferred into a pressurized reactor, the pressure was brought to 1.5 bar using nitrogen, and 581.0 g of propylene oxide (10.0 mol) were metered in at 130° C. in the course of 5 h at a pressure of no more than 5.4 bar. Thereafter, 72.0 g (1.0 mol) of butylene oxide were metered in at 130° C. in 1 h at a pressure of no more than 3.9 bar. After stirring had been continued for 6 h, the mixture was allowed to cool to 80° C. and, while stirring, was flushed with nitrogen. The brown discharge was brought to pH 5.5 using approximately 1.6 g of acetic acid (1% by weight in water) so that 745 g of a pale brown, slightly cloudy product (8) with a yield of 100% were formed.

Example 2

Formulation of Epoxyconazole 5.2 or 10.4 g of epoxyconazole, 7.5 g of surfactant 1, 7.5 g of surfactant 2 and 12.5 g of pyrrolidone alkylene oxide of examples 1 were weighed in and made up to a total volume of 100 ml with ethyl hexyl lactate. The mixture was mixed by stirring at room temperature until a clear homogeneous epoxyconazole solution was obtained.

| Experiments | Amount of epoxyconazole | Pyrrolidone alkylene oxide of example |
|---|---|---|
| A | 5.2 g | 1 A |
| B | 5.2 g | 1 B |
| C | 5.2 g | 1 C |
| D | 10.4 g | 1 A |
| E | 10.4 g | 1 B |
| F | 10.4 g | 1 C |

In each case one sample of experiments A to F was diluted with CIPAC water D (comprising 342 ppm of Ca/Mg ions) to give a 1% by weight emulsion and left to stand for six hours at 20° C. During this time, no epoxyconazole crystals formed.

Example 3

Formulation of Pyraclostrobin 25.2 g of pyraclostrobin, 5.0 g of surfactant 3 and 5.0 g of surfactant 4 were weighed in and made up to a total volume of 100 ml with pyrrolidone alkylene oxide of examples 1. The mixture was mixed by stirring at room temperature until a clear homogeneous pyraclostrobin solution was obtained.

| Experiment | Pyrrolidone alkylene oxide of example |
|---|---|
| A | 1 A |
| B | 1 B |
| C | 1 C |

In each case one sample of experiments A to C was diluted with CIPAC water D (comprising 342 ppm of Ca/Mg ions) to give a 1% by weight emulsion and left to stand for six hours at 20° C. During this time, no pyraclostrobin crystals formed.

Example 4

Formulation of Metconazole 15.2 g of metconazole, 5.0 g of surfactant 3 and 5.0 g of surfactant 4 were weighed in and made up to a total volume of 100 ml with pyrrolidone alkylene oxide of example 1. The mixture was mixed by stirring at room temperature until a clear homogeneous metconazole solution was obtained.

| Experiment | Pyrrolidone alkylene oxide of example |
|---|---|
| A | 1 A |
| B | 1 B |
| C | 1 C |

In each case one sample of experiments A to C was diluted with CIPAC water D (comprising 342 ppm of Ca/Mg ions) to give a 1% by weight emulsion and left to stand for six hours at 20° C. During this time, no metconazole crystals formed.

We claim:

1. A composition comprising a pesticide and polyalkylene oxide, wherein the polyalkylene oxide corresponds to a compound of formula (I)

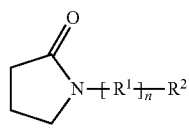

I wherein $R^1$ is —$CH_2$—$CH_2$—O—, propyleneoxy, butyleneoxy and mixtures thereof;
$R^2$ is H and $C_1$-$C_6$-alkyl; and
n has a value from 2 to 20.

2. The composition according to claim 1, comprising at least 10% by weight of pyrrolidone alkylene oxide.

3. The composition according to claim 1, wherein n has a value from 2 to 16.

4. The composition according to claim 1, wherein $R^1$ is butyleneoxy or a mixture of butyleneoxy with ethyleneoxy and/or propyleneoxy.

5. The composition according to claim 1, wherein $R^2$ is H.

6. A process for the preparation of a composition according to claim 1, wherein a pesticide and a pyrrolidone alkylene oxide of the formula I are mixed.

7. A pyrrolidone alkylene oxide of the formula IV

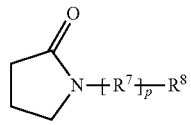

where $R^7$ is butyleneoxy or a mixture of butyleneoxy with —$CH_2$—$CH_2$—O —and/or propyleneoxy;
$R^8$ is H or $C_1$-$C_6$-alkyl; and
p has a value from 2 to 18.

8. A method for controlling phytopathogenic fungi and/or undesired vegetation and/or undesired attack by insects or mites and/or for regulating the growth of plants, comprising allowing a composition of claim 1 to act on the respective pests, their environment or the plants to be protected from the respective pests, on the soil and/or to undesired plants and/or the useful plants and/or their environment.

9. The method of claim 8, wherein said composition comprises at least 10% by weight of pyrrolidone alkylene oxide.

10. The method of claim 8, wherein n has a value from 2 to 16.

11. The method of claim 8, wherein $R^1$ is butyleneoxy or a mixture of butyleneoxy with ethyleneoxy and/or propyleneoxy.

12. The method of claim 8, wherein $R^2$ is H.

13. The method of claim 8, wherein
$R^1$ is propyleneoxy;
$R^2$ is H or $C_1$-$C_6$-alkyl; and
n has a value from 2 to 6.

14. The method of claim 8, wherein
$R^1$ is mixtures of ethyleneoxy and propyleneoxy;
$R^2$ is H or $C_1$-$C_6$-alkyl; and
n has a value from 2 to 12.

15. The method of claim 8, wherein
$R^1$ is butyleneoxy or a mixture of butyleneoxy with —$CH_2$—$CH_2$—O —and/or propyleneoxy;
$R^2$ is H or $C_1$-$C_6$-alkyl; and
n has a value from 2 to 18.

16. A method for controlling undesired attack by insects or mites on plants and/or for controlling phytopathogenic fungi and/or for controlling undesired vegetation, where seeds of useful plants are treated with the composition of claim 1.

17. Seed, treated with the composition of claim 1.

18. The composition of claim 1, wherein said pesticide is soluble in pyrrolidone alkylene oxide to at least 30 g/L at 20° C.

* * * * *